(12) United States Patent
Pelati et al.

(10) Patent No.: US 8,105,969 B2
(45) Date of Patent: Jan. 31, 2012

(54) CATALYST WITH AN ION-MODIFIED BINDER

(75) Inventors: Joseph E Pelati, Houston, TX (US); Taylor Rives, Houston, TX (US)

(73) Assignee: Fina Technology Inc., Houston, TX (US)

( * ) Notice: Subject to any disclaimer, the term of this patent is extended or adjusted under 35 U.S.C. 154(b) by 193 days.

(21) Appl. No.: 12/345,593

(22) Filed: Dec. 29, 2008

(65) Prior Publication Data

US 2010/0167913 A1 Jul. 1, 2010

(51) Int. Cl.
*B01J 29/06* (2006.01)

(52) U.S. Cl. .............. 502/60; 502/63; 502/64; 502/66

(58) Field of Classification Search .............. 502/60, 502/63, 64, 66
See application file for complete search history.

(56) References Cited

U.S. PATENT DOCUMENTS

| | | | |
|---|---|---|---|
| 3,844,935 A * | 10/1974 | Drehman et al. ............... | 208/79 |
| 4,028,227 A | 6/1977 | Gustafson | |
| 4,169,111 A | 9/1979 | Wight | |
| 4,419,271 A * | 12/1983 | Ward ............... | 502/65 |
| 5,196,623 A | 3/1993 | Butler | |
| 5,227,558 A | 7/1993 | Shamshoum et al. | |
| 5,286,693 A * | 2/1994 | Ino et al. ............... | 502/68 |
| 5,600,050 A | 2/1997 | Huang et al. | |
| 5,907,073 A | 5/1999 | Ghosh | |
| 5,990,031 A | 11/1999 | Ghosh | |
| 6,096,675 A | 8/2000 | Resasco et al. | |
| 6,297,417 B1 | 10/2001 | Samson et al. | |
| 6,313,362 B1 | 11/2001 | Green et al. | |
| 6,316,382 B1 * | 11/2001 | Kasztelan ............... | 502/216 |
| 6,355,851 B1 | 3/2002 | Wu et al. | |
| 6,376,729 B1 | 4/2002 | Merrill et al. | |
| 6,440,886 B1 | 8/2002 | Gajda et al. | |
| 6,504,071 B2 | 1/2003 | Zhang et al. | |
| 6,555,492 B2 * | 4/2003 | Faber et al. ............... | 502/65 |
| 6,864,399 B2 | 3/2005 | Merrill et al. | |
| 6,897,346 B1 | 5/2005 | Merrill et al. | |
| 6,987,078 B2 | 1/2006 | Kelly et al. | |
| 7,071,370 B2 | 7/2006 | Harriss et al. | |
| 7,199,275 B2 | 4/2007 | Smith | |
| 7,268,267 B2 | 9/2007 | Jan et al. | |
| 7,276,540 B2 * | 10/2007 | Espinoza et al. ............... | 518/715 |
| 7,297,827 B2 | 11/2007 | Kelly | |
| 7,304,199 B2 | 12/2007 | Xu et al. | |
| 7,371,910 B2 | 5/2008 | Yeh et al. | |
| 7,371,911 B2 | 5/2008 | Butler et al. | |
| 7,393,988 B2 | 7/2008 | Hildreth et al. | |
| 7,405,336 B2 | 7/2008 | Kelly et al. | |
| 7,407,905 B2 | 8/2008 | Ginosar et al. | |
| 7,419,929 B2 | 9/2008 | Kelly et al. | |
| 2004/0132614 A1 * | 7/2004 | Harle et al. ............... | 502/313 |
| 2007/0161838 A1 | 7/2007 | Butler | |
| 2008/0190811 A1 * | 8/2008 | Mao et al. ............... | 208/110 |
| 2008/0242906 A1 | 10/2008 | Butler et al. | |

FOREIGN PATENT DOCUMENTS

| WO | WO 96/33015 | * 10/1996 |
|---|---|---|
| WO | 2006032907 A1 | 3/2006 |

OTHER PUBLICATIONS

Jal., et al. Chemical Modification of Silica Surface by Immobilization of Functional Groups for Extractive Concentration of Metal Ions. Talanta, 2004, vol. 62, pp. 1005-1028.

* cited by examiner

*Primary Examiner* — Elizabeth Wood

(57) ABSTRACT

A solid catalyst, such as a molecular sieve catalyst or solid acid catalyst, is supported by a binder, such as amorphous silica or alumina, wherein the binder is charged with metal ions to form an ion-modified binder. The ion-modified binder is capable of attachment to polar contaminants and inhibit their contact with the catalyst. The catalyst can be a zeolite and can be the catalyst for an alkylation reaction, such as the alkylation of benzene with ethylene.

10 Claims, 2 Drawing Sheets

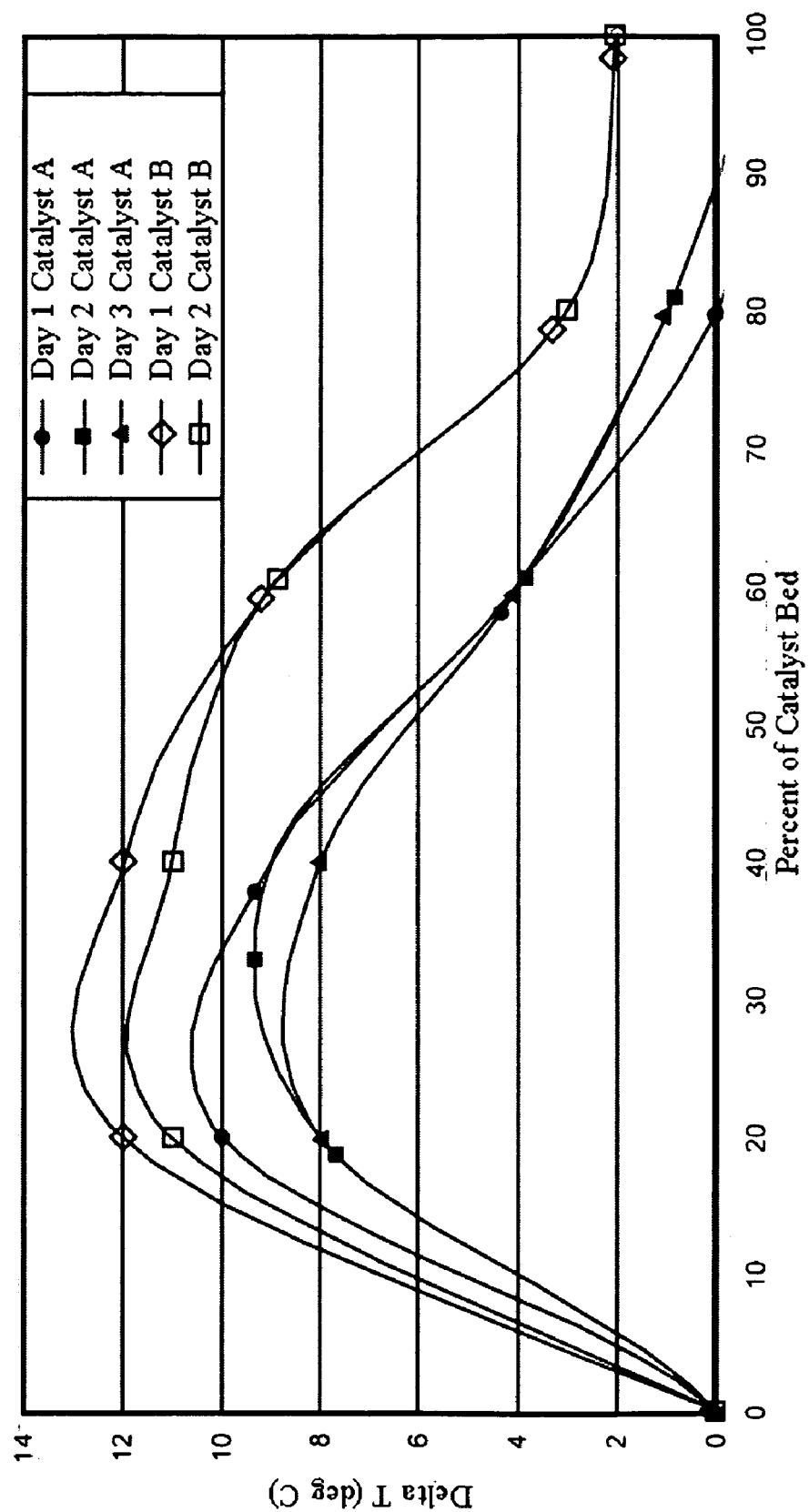

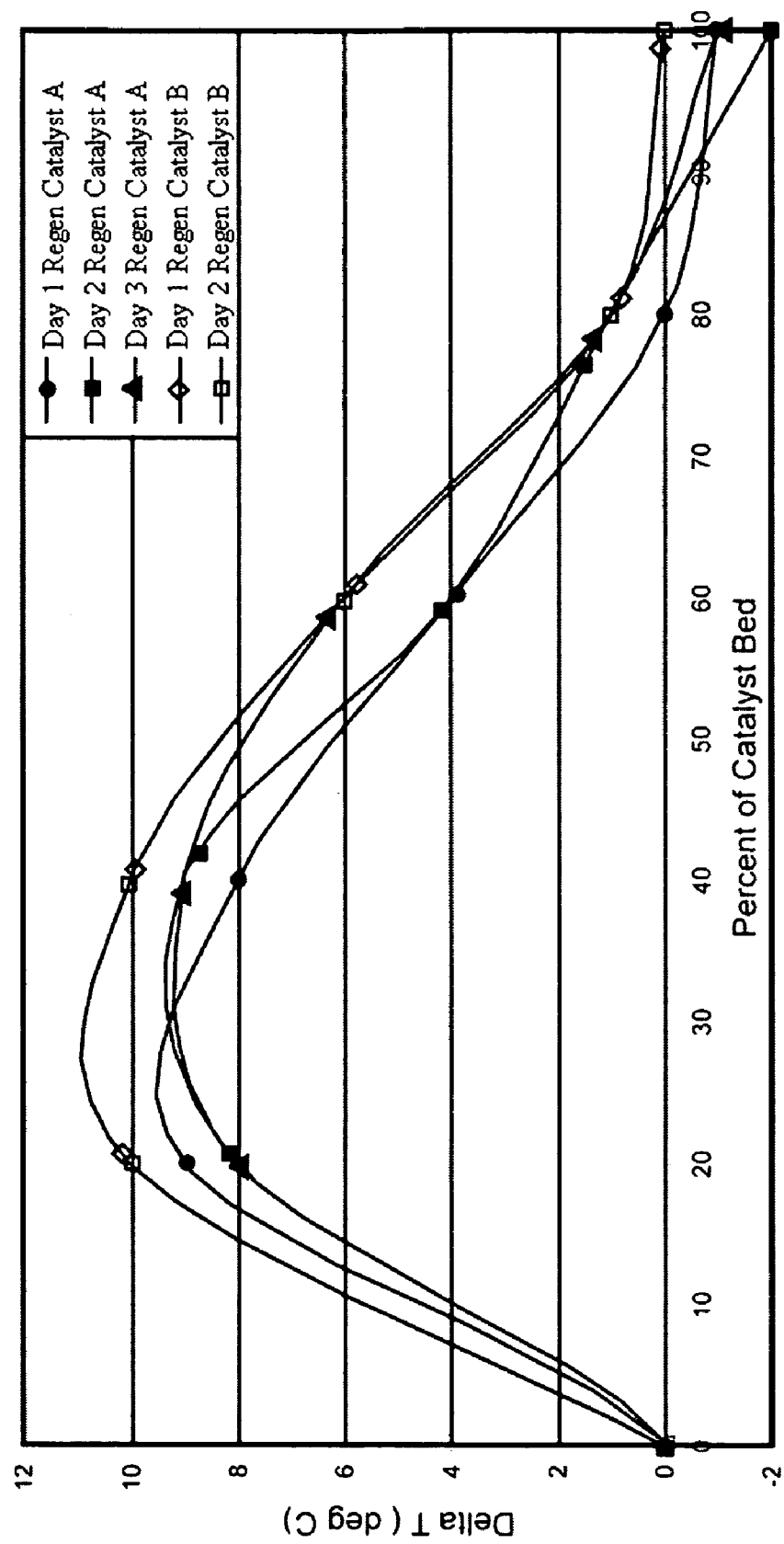

CATALYST WITH AN ION-MODIFIED BINDER

CROSS-REFERENCE TO RELATED APPLICATIONS

Not applicable.

FIELD

The present invention generally relates to binders used with catalysts, such as a zeolite catalyst.

BACKGROUND

Binders can be added to catalytic materials to form an aggregate catalyst with modified properties, such as improved physical properties. One type of catalyst that can be modified with a binder material is a molecular sieve type catalyst such as zeolite.

Zeolite is a crystalline alumino-silicate that is well known for its utility in several applications. It has been used in dealkylation, transalkylation, isomerization, cracking, disproportionation, and dewaxing processes, among others. Its well-ordered structure is composed of tetrahedral $AlO_4^{-5}$ and $SiO_4^{-4}$ molecules bound by oxygen atoms that form a system of pores typically on the order of 3 Å to 10 Å in diameter. These pores create a high internal surface area and allow the zeolite to selectively adsorb certain molecules while excluding others, based on the shape and size of the molecules. Thus, zeolite can be categorized as a molecular sieve. Zeolite can also be termed a "shape selective catalyst." The small pores can restrict reactions to certain transition states or certain products, preventing shapes that do not fit the contours or dimensions of the pores.

The pores in zeolite are generally occupied by water molecules and cations. Cations balance out the negative charge caused by trivalent aluminum cations which are coordinated tetrahedrally by oxygen anions. Zeolite can exchange its native cations for other cations; one example is the exchange of sodium ions for ammonium ions. In some ion-exchanged forms, such as the hydrogen form of zeolite, the catalyst is strongly acidic. The acidic active sites are useful for alkylation as well as many other reactions. For instance, zeolite can serve as a solid acid catalyst for Friedel-Crafts alkylations, replacing traditional aluminum trichloride and other liquid acid catalysts that can be corrosive and damaging to the reactor.

One alkylation reaction for which zeolite can be used as a solid acid catalyst is the alkylation of benzene with ethylene to form ethylbenzene. Ethylbenzene is an aromatic hydrocarbon with the chemical formula $C_6H_5CH_2CH_3$; it consists of a six-carbon aromatic ring with a single attached ethyl group. It can undergo a dehydrogenation reaction to form the monomer styrene, the monomer from which polystyrene is made. Polystyrene is a plastic that can form many useful products, including molded products and foamed products, all of which increase the need for production of styrene's precursor, ethylbenzene.

In the ethylation of benzene, zeolite can be categorized as a heterogenous acid catalyst, because it is in a different phase than the reactants. The zeolite catalyst is solid and usually supported by an alumina or silica binder to increase its mechanical stability inside the reactor bed. The reactants, on the other hand, are either in the liquid, vapor, or supercritical phase. The production of ethyl benzene via alkylation has been done with benzene in the gaseous phase, but it is also possible to use liquid phase alkylation, which requires lower temperatures. Liquid phase alkylation can be more economical in certain situations and can decrease the production of unwanted by-products.

However, operating at the lower temperatures required for liquid phase alkylation can have the effect of increasing the catalyst's sensitivity to impurities in the feedstock. The acid sites in zeolite are prone to deactivation, especially in liquid phase reactions, by polar molecules containing nitrogen, oxygen, and sulfur functional groups. The deactivation of the catalyst's acid groups decreases catalyst efficiency. One result can be that the catalyst's deactivation rate increases, necessitating more frequent catalyst regeneration and shortening the overall lifetime of the catalyst. Catalyst regeneration and replacement can both require process shutdown of the reactors, costing time and money, and thus it is desirable to perform these functions infrequently.

One solution has been to filter polar poisons from the feedstock prior to its contact with the zeolite catalyst, such as by passing the feed stream through one or more molecular sieves prior to its entering the main reaction bed. In many cases, however, trace amounts of these polar contaminants still reach the zeolite catalyst.

Because the present technology for purifying the alkylation feedstock fails to entirely prevent small amounts of polar contaminants from entering the reaction bed, it would be desirable to inhibit the contaminants that do enter the reaction bed from contacting the active sites of the zeolite catalyst. It is desirable to inhibit contaminants from contacting the active sites of the catalyst, whether zeolite or other catalyst types.

SUMMARY

Embodiments of the present invention generally include a catalyst that employs a binder as a means of mechanical support, wherein the binder is modified by the inclusion of metal ions to form an ion-modified binder. The ion-modified binder can attach to polar contaminants present in the reaction bed in such a way that inhibits contact between the polar contaminants and the catalyst. The ion-modified binder can attach to the contaminants without adversely affecting the catalyst or causing significant by-product formation at reaction conditions. Furthermore, the ion-modified binder can lengthen the overall catalyst life and decrease the rate of deactivation of the catalyst by preventing the contact of polar contaminants with the catalyst.

The ion-modified binder can comprise amorphous silica or alumina. The silica or alumina becomes "ion-modified" by the addition of metal ions or similar species. One method of adding metals ions to a binder is incipient wetness impregnation. The metal ions can make up from 0.1% to 50%, optionally from 0.1% to 20%, optionally from 0.1% to 5%, by weight of the ion-modified binder. Suitable metal ions include Co, Fe, Cu, Zn, Sn, Pb, Bi, Ba, V, Mn and similar species such as metal oxides, nanoparticles, or mixed metal oxide phases, and combinations thereof. Any metal ions, similar species, or combinations thereof that can enable a binder to absorb polar contaminants can be useful for the present invention.

The ion-modified binder can make up from 1% to 80%, optionally from 5% to 60%, optionally from 10% to 30%, by weight of the catalyst. Aggregates consisting of a catalyst and an ion-modified binder can be formed by mixing the catalyst and binder in the presence of volatiles and shaping the mixture via extrusion or other means to form a shape suitable for a reaction bed. The shaped form can be dried at temperature of from 100° C. to 200° C. and can be calcined at a temperature of from 400° C. to 1000° C. in a substantially dry environment.

The catalyst formed with the ion-modified binder falls into either of the general categories comprising molecular sieve catalysts and solid acid catalyst. The catalyst can be a zeolite. The catalyst can be used in many reactions, including alkylation, dealkylation, transalkylation, isomerization, cracking, disproportionation, dewaxing, and aromatization.

Alkylation reactions can take place between an aromatic substrate and an alkylating agent. In one embodiment the aromatic substrate is benzene and the alkylating agent is ethylene. The present invention can be applied towards the alkylation of benzene with ethylene, wherein ethylene and benzene are introduced into a reaction bed housing a zeolite catalyst formed with an ion-modified binder. A reaction takes place forming ethylbenzene as its main product. The alkylation can be vapor phase, liquid phase, or supercritical phase. The ethylene and benzene feed streams can be pretreated prior to their introduction to the reaction bed; however, polar contaminants may still be present in the feed stream. Polar contaminants that enter the reaction bed can be absorbed by the ion-modified binder.

An alternate embodiment of the present invention is a method for preparing a catalyst that includes adding metal ions to a binder to form an ion-modified binder and combining the ion-modified binder with the catalyst to form an ion-modified binder and catalyst aggregate. The catalyst can be used in a reaction bed for the alkylation of benzene with ethylene. The catalyst can be a zeolite catalyst, and the binder can be modified with ions via an incipient wetness method.

The metal ions can make up 0.1% to 50% by weight of the ion-modified binder. The ion-modified binder can make up 1% to 80% by weight of the catalyst. The metal ions can be chosen from the group consisting of Co, Fe, Cu, Zn, Sn, Pb, Bi, Ba, Mn and V, and combinations thereof. The ion-modified binder can be capable of attachment to polar contaminants and thereby inhibit the contact of polar contaminants with the zeolite.

BRIEF DESCRIPTION OF DRAWINGS

FIG. 1 charts the temperature differentials of adjacent thermocouples along a reactor bed using a zeolite catalyst with an unmodified binder.

FIG. 2 charts the temperature differentials of adjacent thermocouples along a reactor bed using a zeolite catalyst with an ion-modified binder.

DETAILED DESCRIPTION

The present invention relates to the modification of a binder for a catalyst, such as a zeolite catalyst, to inhibit interaction of polar contaminants in the reaction bed with the catalyst. Specifically, the binder is modified by the addition of active metal ions, or other similar species, to capture the polar contaminants in a way that inhibits the contaminants from contacting the catalyst and inhibits by-product formation.

The powder form of zeolite and other catalysts can be unsuitable for use in the reactor, due to a lack of mechanical stability, making alkylation and other desired reactions difficult. To render a catalyst suitable for the reactor, it can be combined with a binder to form an aggregate, such as a zeolite aggregate, with enhanced mechanical stability and strength. The aggregate can then be shaped or extruded into a form suitable for the reaction bed. The binder can desirably withstand temperature and mechanical stress and ideally does not interfere with the reactants adsorbing to the catalyst. It is possible for the binder to form macropores, much greater in size than the pores of the catalyst, which can provide improved diffusional access of the reactants to the catalyst.

Binder materials that are suitable for the present invention include, but are not limited to, silica, alumina, titania, zirconia, zinc oxide, magnesia, boria, silica-alumina, silica-magnesia, chromia-alumina, alumina-boria, silica-zirconia, silica gel, clays, similar species, and any combinations thereof. The most frequently used binders are amorphous silica and alumina, including gamma-, eta-, and theta-alumina. It should be noted that a binder can be used with many different catalysts, including various forms of zeolite and non-zeolite catalysts that require mechanical support.

According to the present invention, the binder is modified such that it provides mechanical support and performs other typical functions of a binder, as well as limiting the contact of polar contaminants with the catalyst. The binder of the present invention is composed of alumina or silica or similar amorphous material and includes active metal ions or similar species. The active metal ions may be ions of the following non-limiting examples of Co, Fe, Cu, Zn, Sn, Pb, Bi, Ba, V, Mn, or similar species such as metal oxides, nanoparticles, or mixed metal oxide phases. Other similar metal ions and species not listed may be used, as well as combinations of any of the listed and unlisted metal ions and similar species.

As used herein, the term "metal ion" is meant to include all active metal ions and similar species, such as metal oxides, nanoparticles, and mixed metal oxide phases, capable of being added to a binder and enabling said binder to attach to polar contaminants without adversely affecting the catalyst that it supports or causing significant by-product formation at reaction conditions. Further, the term "ion-modified binder" as used herein refers to a binder for a catalyst that has been modified with a metal ion to attach to polar contaminants. It is desirable that the metal ions not adversely affect the catalyst that it supports or cause significant by-product formation to occur. Polar contaminants generally include polar molecules such as those with nitrogen, oxygen, and sulfur functional groups. Typical polar contaminants encountered in the liquid phase alkylation of benzene with ethylene include amines, nitriles, aldehydes, alcohols, acids, sulfur species, and the like. These and similar species can also be contaminants for reactions other than the alkylation of benzene with ethylene.

The metal ion can be added to the binder in the amount of 0.1% to 50%, optionally 0.1% to 20%, optionally 0.1% to 5%, by weight of the binder. The metal ion can be added to the binder by any means known in the art. Generally, the method used is incipient wetness impregnation, wherein the metal ion precursor is added to an aqueous solution, which solution is poured over the binder. After sitting for a specified period, the binder is dried and calcined, such that the water is removed with the metal ion deposited on the binder surface. The ion-modified binder can then be mixed with a catalyst by any means known in the art. The mixture is shaped via extrusion or some other method into a form such as a pellet, tablet, cylinder, cloverleaf, dumbbell, symmetrical and asymmetrical polylobates, sphere, or any other shape suitable for the reaction bed. The shaped form is then usually dried and calcined. Drying can take place at a temperature of from 100° C. to 200° C. Calcining can take place at a temperature of from 400° C. to 1000° C. in a substantially dry environment. The resultant catalyst aggregate can contain ion-modified binder in concentrations of from 1% to 80%, optionally from 5% to 50%, optionally from 10% to 30%, by weight. The percent weight of the catalyst that is binder is somewhat determined by the temperature of the reaction zone in which the catalyst will be used. For example, in the use of zeolite for an alkylation reaction, about 50% zeolite and 50% binder can be used in the higher temperature alkylation catalyst beds and about 75% zeolite and 25% binder can be used in the lower temperature alkylation catalyst beds.

For the present invention, the catalyst to be supported and protected by the ion-modified binder can be a zeolite, but can also be a non-zeolite. Zeolite is generally a porous, crystalline alumino-silicate, and it can be formed either naturally or synthetically. One method of forming synthetic zeolite is the hydrothermal digestion of silica, alumina, sodium or other alkyl metal oxide, and an organic templating agent. The amounts of each reactant and the inclusion of various metal oxides can lead to several different synthetic zeolite compositions. Furthermore, zeolite is commonly altered through a variety of methods to adjust characteristics such as pore size, structure, activity, acidity, and silica/alumina molar ratio. Thus, a number of different forms of zeolite are available. Different classes of zeolite and zeolite-like catalysts include the types zeolite A, zeolite X, zeolite Y, zeolite L, zeolite beta, zeolite omega, zeolite Z, ZSM-3, ZSM-4, ZSM-5, ZSM-11, ZSM-12, ZSM-18, ZSM-20, ZSM-22, ZSM-23, ZSM-35, ZSM-38, ZSM-48, ZSM-50, MCM-22, MCM-36, MCM-49, MCM-56, MCM-58, MCM-68, ITQ-1, ITQ-2, PSH-3, SSZ-25, ERB-1, ERB-3, NU-10, Theta 1, TS-1, as well as faujasite, mordenite, chabazite, offretite, clinoptilolite, erionite, sihealite, and the like. It is possible to generate crystals that are not alumino-silicates but behave similarly to zeolite, including aluminophosphates such as ALPO-5 and VPI-5, metalosilicophosphates, silicoaluminophosphates such as SAPO-5, SAPO-31, SAPO-34, SAPO-37, SAPO-40, and SAPO-41, porous crystalline magnesium silicates, and tungstate modified zirconia. Other elements, including boron, gallium, iron and germanium, have also been used to replace the aluminum or silicon in the framework structure of zeolite.

Another method of altering zeolite is by ion-exchange. For example, the hydrogen form of zeolite can be produced by ion-exchanging beta zeolite with ammonium ions. Metal ions can also be incorporated into zeolite, either by ion-exchange or another method. Examples of such metal ion promoters include cerium, lanthanum, and other metals from the lanthanide series. It has also been reported that "as-synthesized" Na zeolite can be ion-exchanged to include IA, IIA or IIIA metals, such as ions of lithium, potassium, calcium, magnesium, lanthanum, cerium, nickel, platinum, palladium, and the like. Other metals that may be used with zeolite include those from the groups IIB, III, IV, V, VI, VIIA and VIII, and the like. Specific non-limiting examples include Group IIA (Mg, Ca, Sr, Ba), Group IIIA (B, Al, Ga, In), Group IIIB (Sc, Y, and the lanthanide elements), Group IVB (Ti, Zr, Hf), Group VB (V, Nb, Ta), Group VIB (Cr, Mo, W), and Group VIIB (Mn, Tc, Re) of the Periodic Table of the Elements. Halogens are also possible inclusions in the zeolite framework. Further, the silica/alumina ratio of the zeolite can be altered, via a variety of methods, such as dealumination by steaming or acid washing to increase the silica/alumina ratio. Increasing the amount of silica relative to alumina can have the effect of increasing the catalyst hydrophobicity. The silica/alumina ratio can range from less than 0.5 to 500 or greater. Some catalysts other than zeolite can also be used with a binder of the present invention, including catalysts that fall into the general categories of molecular sieves and/or solid acid catalysts.

Thus, a variety of zeolites and non-zeolites are available for use in conjunction with the ion-modified binder of the present invention. The various catalysts listed in the two preceding paragraphs are not meant to be an exhaustive list, but is meant to indicate the type of catalysts for which an ion-modified binder can be useful. The choice of catalyst will depend on the reaction type and the reaction conditions in which it will be used. One skilled in the art can select any zeolite or non-zeolite catalyst that meets the needs of the intended reaction, provided that an ion-modified binder can be used to support the catalyst and inhibit polar contaminants from interfering with the catalyst.

Processes for which an ion-modified binder can be used include, but are not limited to, oxidation, reduction, adsorption, dimerization, oligomerization, polymerization, etherification, esterification, hydration, dehydration, condensation, acetalization, dealkylation, cyclization, alkylation, hydrodealkylation, exhaust gas cleaning, transalkylation, isomerization, cracking, disproportionation, dewaxing, hydroisomerization, hydrocracking, aromatization, and any process employing a molecular sieve or solid acid catalyst in which contact between the catalyst and polar contaminants is wished to be reduced. One common process is alkylation.

Many different forms of alkylation reactions are possible. In general, alkylation occurs when an alkylating agent consisting of one or more carbon atoms is added to an alkylatable substrate. Alkylating agents that can be used in alkylation reactions are generally olefins. An olefin can be short chain, like ethylene, propylene, butene, and pentene, or it can be long chain with a higher number of carbon atoms. It can be an alpha olefin, an isomerized olefin, a branched-chain olefin or a mixture thereof. Alkylating agents other than olefins include alkynes, alkyl halides, alcohols, ethers, and esters. In some cases, the alkylating agent is diluted with a diluting agent prior to its introduction into the reaction bed. Especially for ethylene, diluting agents such as inert, or nonreactive, gases like nitrogen have been reported, with the concentration of the diluting agent greater than the concentration of the alkylating agent in the diluted feedstream, optionally around 70% diluting agent and 30% alkylating agent.

The alkylatable substrate is usually an unsaturated hydrocarbon or an aromatic. If the alkylatable substrate is an aromatic compound, it can be unsubstituted, monosubstituted, or polysubstituted, and it possesses at least one hydrogen atom bonded directly to the aromatic nucleus or some other site that will allow for alkylation to occur. The aromatic nucleus can be benzene or a compound comprising more than one aromatic ring, like naphthalene, anthracene, naphthacene, perylene, coronene, and phenanthrene. Compounds that have an aromatic character but contain a heteroatom in the ring can also be used, provided they will not cause unwanted side reactions. Substituents on the aromatic nucleus can be alkyl, hydroxy, alkoxy, aryl, alkaryl, aryloxy, cycloalkyl, halide, and/or other groups which do not interfere with the alkylation reaction and that comprise 1 to 20 carbon atoms. Aromatic substrates that may be alkylated by an alkylating agent include toluene, xylene, biphenyl, ethylbenzene, isopropylbenzene, normal propylbenzene, butylbenzene, pentylbenzene, hexylbenzene, heptylbenzene, octylbenzene, nonylbenzene, dodecylbenzene, pentadecylbenzene, hexyltoluene, nonyltoluene, dodecyltoluene, pentadecytoluene, alpha-methylnaphthalene, mesitylene, durene, cymene, pseudocumene, diethylbenzene, isoamylbenzene, isohexylbenzene, pentaethylbenzene, pentamethylbenzene, tetraethylbenzene, tetramethylbenzene, triethylbenzene, trimethylbenzene, butyltoluene, diethyltoluene, ethyltoluene, propyltoluene, dimethylnaphthalenes, ethylnaphthalene, dimethylanthracene, ethylanthracene, methylanthracene, dimethylphenanthrene, phenanthrenephenol, cresol, anisole, ethoxybenzene, propoxybenzene, butoxybenzene, pentoxybenzene, hexoxybenzene, any isomers thereof, and the like.

One common alkylation reaction towards which the present invention can be applied is the alkylation of benzene with propylene to produce cumene.

Another common alkylation reaction for which the present invention is useful is the alkylation of benzene with ethylene over a solid acid catalyst. Reactants for the ethylation of benzene generally include ethylene as the alkylating agent and benzene as the alkylatable substrate. The source of both reactants is generally refined petroleum, but each can come from other sources as well. Depending on the source, the reactants may have varying levels of purity. Ethylene is generally recovered from hydrocarbon cracking and goes through repeated cycles of distillation until a desired level of purity is obtained. The purity may be as high as or higher than polymer grade ethylene, 99.5%. However, less pure or diluted ethylene can be used. For example, dilute ethylene can contain 50% or more impurities, which can be made up of mostly ethane and a small amount of hydrogen or methane. As previously mentioned, ethylene can also be diluted with an inert gas. Both ethylene and benzene can be diluted with diluents such as ethane, mixed hexanes, mixed butanes, and the like. The purity level of benzene can vary as well. Most prior art teachings suggest a purity greater than 90%, optionally 98% or more. The contaminants in the benzene feed stream can include toluene, ethylbenzene, and C-7 hydrocarbons that are not easily separated from benzene.

The feed stream containing the reactants can be treated for the removal of contaminants prior to its introduction into the reaction bed. Various forms of feed stream pretreatment can remove contaminants such as olefins, diolefins, styrene, oxygenated organic compounds, sulfur-containing compounds, nitrogen-containing compounds, and oligomeric compounds. One method is the use of a large pore molecular sieve catalyst to remove impurities prior to the alkylation reaction. The molecular sieve can be placed, for example, in a reactive guard bed, in which the alkylation reaction occurs along with the capture of contaminants. This reactive guard bed can be equipped with a by-pass, so that the molecular sieve can undergo regeneration without interrupting the reaction in the main alkylation reactor beds. Despite pretreatment, some polar contaminants may still reach the reaction bed.

The reactants ethylene and benzene can enter the reactor via a single inlet or separate inlets. The reactants can be delivered to the reaction bed in the gaseous phase, the liquid phase, a combination of liquid and gaseous phase, the supercritical phase, or a combination of liquid and supercritical phases. The reaction conditions, including reactor type, pressure, temperature, liquid hourly space velocity (LHSV), and benzene to ethylene ratio depend in part on the phase in which the alkylation is to occur.

For vapor phase alkylation, the reactions conditions generally include a temperature of from about 270° C. to 400° C., a pressure of from about 200 psig to 600 psig, a LHSV of from about 10 $hr^{-1}$ to 70 $hr^{-1}$, and a benzene to ethylene ratio of from about 3:1 to 20:1. Further, gas phase alkylation is generally performed with a reactor operated in a down-flow mode but can use another flow type.

For liquid phase alkylation, the reaction zone is operated at such temperature and pressure to maintain essentially liquid phase conditions. For the production of ethylbenzene, the reaction temperature may range from about 40° C. to 320° C., and is generally between about 120° C. and 280° C. The alkylation pressure is generally kept high enough to ensure a liquid phase. In one embodiment the pressures can range from 300 psig to 1600 psig, or up to 3000 psig, in an alternate embodiment the pressures can range from 500 psig to 1000 psig. Flow rates typically can range from liquid hourly space velocity (LHSV) between about 1 and 100 $hr^{-1}$ per bed and an aromatic benzene to ethylene molar ratio between about 1:1 and 100:1. In one embodiment LHSV's between about 10 to 70 $hr^{-1}$ per bed and benzene to ethylene molar ratios between about 2:1 to 50:1 are used. In another embodiment an LHSV of from about 10 $hr^{-1}$ to 70 $hr^{-1}$, and a benzene to ethylene molar ratio of from about 3:1 to 20:1 can be used. Further, liquid phase alkylation is generally performed with an up-flow reactor but can be performed with another flow type. If the pressure is not high enough, the reactants, in particular benzene, can be partially in the liquid phase and partially in the vapor phase.

For supercritical phase alkylation, the reaction conditions generally include pressure and temperature conditions which are above the critical point for benzene. Specifically, the temperature in the alkylation zone is at or above 280° C., and the pressure is at or above 550 psig. In general, the reaction conditions can involve a temperature of from about 300° C. to 600° C., a pressure of from about 550 psia to 850 psia, a LHSV of from about 10 $hr^{-1}$ to 150 $hr^{-1}$, and benzene to ethylene ratio of from about 1:1 to 15:1. Under such conditions, it is possible to have some benzene present in both the liquid and the supercritical phases.

In general, the reactor scheme can be any one that is known in the art to be useful. For instance, either a single stage reactor or a multiple stage reactor with several reactor beds in series can be used. For multiple stage reactors, it is possible to have interstage injection of ethylene and benzene, as well as interstage cooling, between catalyst beds. A reactor can have an upward flow, a downward flow, or a horizontal flow configuration. The reaction beds can be fixed, swing, moving, or some other type. The reactor optionally can include heat exchangers, thermocouples, or any other supplemental devices known in the art to be useful. It can include an outlet for the reaction products. This outlet can to lead to a separation and recovery zone, in which ethylbenzene and other effluents like unreacted ethylene or benzene and diethyl and polyethyl benzene are separated, generally by distillation. A recycle stream can be included for certain products, such as diethylbenzene and polyethylated benzenes, to either return to the main reactor bed or be introduced into a new reactor for transalkylation. Transalkylation is a reaction in which the alkylatable substrate, in this case benzene, and polyalkylated effluent, in this case polyethyl benzene, react over a molecular sieve or solid acid catalyst like zeolite to form monoalkylated effluent, in this case ethylbenzene. Transalkylation reactions can be performed in either liquid or vapor phase and can use either the same or a different catalyst from the alkylation catalyst.

After a period of running the alkylation reactions, deactivation of the catalyst can occur. Catalyst deactivation can be due to coke formation on the catalyst bed, which is in part due to the exothermic nature of the alkylation reaction. The degree of deactivation can be determined in part by measuring the exotherm as it moves through the catalyst bed from the inlet side to the outlet side of the reactor. Exotherm can be measured, for instance, by measuring the temperature differentials between adjacent thermocouples placed along the reaction bed. Another cause of catalyst deactivation can be the polymerization of the olefinic alkylating agent, ethylene. The large oligomers cannot diffuse out of the pores containing the active sites in the zeolitic material and can cause the zeolite to lose its catalytic activity. Deactivation can also be caused by the polar contaminants which have been previously discussed and are the target of the ion-modified binder of this invention.

Zeolite deactivation generally requires a regeneration procedure to be performed. Some methods of regenerating zeolite include heating to remove adsorbed materials, ion exchanging with sodium to remove unwanted cations, or pressure swing to remove adsorbed gases. One solution involves flushing the catalyst with benzene. Other solutions generally involve processing the catalyst at high temperatures using regeneration gas and oxygen. According to one procedure, a zeolite beta can be regenerated by heating the catalyst first to a temperature in excess of 300° C. in an oxygen-free environment. Then an oxidative regeneration gas can be supplied to the catalyst bed with oxidation of a portion of a relatively porous coke component to produce an exotherm moving through the catalyst bed. Either the temperature or the oxygen content of the gas can be progressively increased to oxidize a porous component of the coke. Again, regeneration gas can be supplied, wherein the gas has either increased oxygen content or increased temperature to oxidize a less porous refractory component of the coke. The regeneration process can be completed by passing an inert gas through the catalyst bed at a reduced temperature. One benefit of the ion-modified binder of the present inventions can be that oxygen-activating metal ions, if present in the binder, can enhance regeneration.

In one aspect, the present invention is for a zeolite catalyst for ethylbenzene alkylation, wherein the zeolite is supported by an ion-modified binder. In another aspect, the present invention is for a binder for a molecular sieve or solid acid catalyst, wherein said binder is ion-modified such that it inhibits polar contaminants in the reaction bed from reaching said catalyst and does not result in significant by-product formation at reaction conditions. In another aspect, the present invention is a method of preparing a zeolite catalyst with an ion-modified binder, comprising the steps of: adding an amount of metal ion to a binder via incipient wetness impregnation, mixing the ion-modified binder with zeolite catalyst to form a catalyst aggregate, shaping the catalyst aggregate into a shape suitable for an alkylation reactor bed, and drying and calcining the shaped catalyst aggregate. In still another aspect, the present invention is a method for the production of ethylbenzene, comprising the steps of: contacting ethylene with benzene in the presence of a zeolite catalyst in a liquid phase reaction zone, wherein said zeolite is supported by an ion-modified binder; and recovering ethylbenzene effluent from the reaction zone.

Zeolite catalysts prepared with an ion-modified binder can show improved catalytic performance and catalyst lifetime. Further, the deactivation rate and by-product formation can be reduced. These improvements can occur as a result of decreased contact between the catalyst and polar contaminants. The following example demonstrates the properties of a zeolite catalyst supported by an ion-modified binder and exemplifies the methods for producing said binder and said catalyst. This example is not meant to reduce the scope of the present invention, but merely describe one particular embodiment.

Two zeolite catalysts were prepared, both employing alumina binders. In one catalyst, the alumina was modified by adding cobalt nitrate via incipient wetness impregnation to the alumina to form an ion-modified binder. The other catalyst was formed with an unmodified binder in order to serve as a reference. Other than the addition of cobalt ions to the binder of one of the catalysts, the two catalysts were prepared using the same ingredients and procedures. Herein, the reference catalyst shall be referred to as "catalyst A", while the catalyst containing an ion-modified binder shall be referred to as "catalyst B".

The reference catalyst, or catalyst A, was prepared by placing 24 g of Z-SAR300 H-beta powder and 6 g of gamma alumina (Alfa Aesar #39812, 3 micron, 80-120 m$^2$/g) in a beaker and mixing. To the same beaker 0.3 g of graphite powder was added and mixed in. Water was poured into a separate beaker containing 1.25 g of sugar until a total mass of 5 g was reached, to form a 25% aqueous sugar solution. The sugar solution was added drop wise to the beaker containing the zeolite and alumina powder until a viscous solution of a consistency similar to cake mix formed. A 13 mm die and a Carver press were used to form pellets from the viscous solution. The pellets were then calcined by placing them in a ceramic dish in a calcining furnace, at ~115° C. for one hour initially. At the end of the hour, the temperature was increased by 50° C. every 30 minutes until a temperature of 500° C. was reached, at which point the temperature was held constant for two hours. The catalyst was then removed from the furnace, cooled, and stored in a sealed bottle. Later, the catalyst was crushed and sieved to a 40-60 mesh for use in the alkylation reactor.

The other catalyst, catalyst B, was prepared according to the same procedure, except that 6 g of an ion-modified binder was used in the place of 6 g of unmodified gamma alumina. The ion-modified binder was 0.5% Co on gamma alumina. It was prepared by adding 0.49 g of Co(NO$_3$)$_2$-6aq to 16.1 mL of deionized water in a beaker and stirring until dissolved. The solution was added a few drops at a time to another beaker containing 20 g of dry gamma alumina, all the while mixing well. The mixture was left open to the atmosphere for two hours. The mixture was dried overnight at 100-120° C. After drying, the binder was calcined at 450° C. for four hours and crushed and sieved to less than 350 mesh. The resultant ion-modified binder was then used to prepare a zeolite catalyst according to the same procedure as described in the preceding paragraph.

Catalysts A and B were evaluated in a laboratory reactor for the liquid phase alkylation of benzene with ethylene. A 10 mL catalyst bed packed with 40-60 mesh of the catalyst was loaded into a tubular up-flow reactor. The experimental conditions were 72 hr$^{-1}$ LHSV, an 18 molar ratio of benzene to ethylene, a pressure of 500 psig, a temperature of 200° C. for the benzene flow, and daily gas chromatography analysis. The reaction was monitored by observing the exotherm using thermocouples placed at 20% sections of the catalyst bed. The exotherm created in each zone was estimated by temperature difference (delta T) in adjacent thermocouples. The data from the initial run of catalysts A and B is shown in FIG. 1 and is included in Table 1.

FIG. 1 illustrates the temperature differential of adjacent thermocouples placed along the catalyst bed. Percent of catalyst bed appears on the x-axis and delta T in ° C. appears on the y-axis. The exotherm of the zeolite catalyst is estimated by the temperature differentials of adjacent thermocouples and is represented by the curves appearing in the chart.

As indicated by FIG. 1, both catalysts were active during all days of operation. Catalyst B achieved a greater exotherm than did catalyst A on both the first and second days of operation. The larger, broader exotherm for catalyst B could be due to slightly elevated ethylene flow.

Further, both catalysts show some amount of deactivation on the second day of operation, as indicated by the difference in exotherm between the first and second days of operation. Catalyst B shows less of difference in exotherm between the first and second day than does Catalyst A, indicating that catalyst B experienced less deactivation on the second day than did catalyst A. Thus, a zeolite catalyst containing an ion-modified binder can be more resistant to deactivation than a zeolite catalyst containing an unmodified binder.

Not indicated by FIG. 1, was that on the second day, the reference catalyst A produced 5.3% diethylbenzene (DEB) relative to ethylbenzene, while catalyst B produced only 3.1%. DEB and other polyalkylated benzenes are by-products commonly produced from the alkylation of benzene. It is generally desirable to reduce the number of such by-products and to maximize the percent of products leaving the reaction bed that are the desired product, ethylbenzene. Catalyst B, with its ion-modified binder, produced less DEB by-product than did catalyst A, showing better selectivity along with its slower rate of deactivation.

Catalysts A and B were regenerated in the reactor using diluted air (2%) at 510° C. A benefit of the ion-modified binder is that regeneration can be improved if the added metal ions can activate oxygen. Cobalt is one metal known to have such properties. After regeneration, alkylation reactions were repeated, according to the same reaction conditions as before. The results are displayed in FIG. 2 and included in Table 1.

FIG. 2 is a chart, similar to FIG. 1, which illustrates the temperature differential of adjacent thermocouples along the catalyst bed. Percent of catalyst bed appears on the x-axis and delta T in ° C. appears on the y-axis. The exotherm of the zeolite catalyst is estimated by the temperature differentials of adjacent thermocouples and is represented by the curves appearing in the chart. According to FIG. 2, both catalysts were active on all days of operation after undergoing regeneration. For catalyst A, the difference in the exotherm between the first and second days of operation was moderate, indicating a moderate level of deactivation. For catalyst B, the difference in the exotherm between the first and second days of operation was minimal, indicating a very low level of, if not zero, deactivation.

The percent of DEB produced on the second day was 4.1% for catalyst A, and 3.2% for catalyst B. The experiments after regeneration indicate again that catalyst B is more selective and more resistant to deactivation than is catalyst A.

The experimental data for catalysts A and B are listed in Table 1, temperatures and temperature differentials are in ° C.

TABLE 1

Catalyst A

| | Initial Runs | | | Regenerated Runs | | |
|---|---|---|---|---|---|---|
| | Day 1 | Day 2 | Day 3 | Day 1 | Day 2 | Day 3 |
| TE 105 C. | 226 | 224 | 222 | 223 | 223 | 225 |
| TE 106 C. | 227 | 225 | 223 | 224 | 225 | 226 |
| TE 107 C. | 227 | 224 | 222 | 224 | 224 | 225 |
| TE 108 C. | 223 | 220 | 218 | 220 | 220 | 219 |
| TE 109 C. | 214 | 211 | 210 | 212 | 211 | 210 |
| TE 110 C. | 204 | 203 | 202 | 203 | 203 | 202 |
| Temperature Differentials | | | | | | |
| 0 | 0 | 0 | 0 | 0 | 0 | 0 |
| 20 | 10 | 8 | 8 | 9 | 8 | 8 |
| 40 | 9 | 9 | 8 | 8 | 9 | 9 |
| 60 | 4 | 4 | 4 | 4 | 4 | 6 |
| 80 | 0 | 1 | 1 | 0 | 1 | 1 |
| 100 | −1 | −1 | −1 | −1 | −2 | −1 |

Catalyst B

| | Initial Runs | | Regenerated Runs | |
|---|---|---|---|---|
| | Day 1 | Day 2 | Day 1 | Day 2 |
| TE 105 C. | 224 | 220 | 217 | 216 |
| TE 106 C. | 222 | 218 | 217 | 216 |
| TE 107 C. | 219 | 215 | 216 | 215 |
| TE 108 C. | 210 | 206 | 210 | 209 |
| TE 109 C. | 198 | 195 | 200 | 199 |
| TE 110 C. | 186 | 184 | 190 | 189 |
| Temperature Differentials | | | | |
| 0 | 0 | 0 | 0 | 0 |
| 20 | 12 | 11 | 10 | 10 |
| 40 | 12 | 11 | 10 | 10 |
| 60 | 9 | 9 | 6 | 6 |
| 80 | 3 | 3 | 1 | 1 |
| 100 | 2 | 2 | 0 | 0 |

According to the example given, the use of an ion-modified binder to absorb polar contaminants can improve catalytic performance and lifetime, and can also reduce the deactivation rate and by-product formation. Additionally, the use of oxygen-activating metal ions in the ion-modified binder can enhance regeneration. The use of an ion-modified binder according to the present invention can be applied to any process involving zeolite catalysts, molecular sieve catalysts, and solid acid catalysts that are prone to contamination by polar molecules. Many parameters such as reaction type, zeolite type, and reaction conditions may be altered without departing from the scope of the invention.

The term "deactivated catalyst" refers to a catalyst that has lost enough catalyst activity to no longer be efficient in a specified process. Such efficiency is determined by individual process parameters.

The term "ion-modified binder" as used herein refers to a binder for a catalyst that has been modified with a metal ion.

The term "molecular sieve" refers to a material having a fixed, open-network structure, usually crystalline, that may be used to separate hydrocarbons or other mixtures by selective occlusion of one or more of the constituents, or may be used as a catalyst in a catalytic conversion process.

Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

The term "regenerated catalyst" refers to a catalyst that has regained enough activity to be efficient in a specified process. Such efficiency is determined by individual process parameters.

The term "regeneration" refers to a process for renewing catalyst activity and/or making a catalyst reusable after its activity has reached an unacceptable/inefficient level. Examples of such regeneration may include passing steam over a catalyst bed or burning off carbon residue, for example.

The term "transalkylation" refers to the transfer of an alkyl group from one aromatic molecule to another.

The term "zeolite" refers to a molecular sieve containing a silicate lattice, usually in association with some aluminum, boron, gallium, iron, and/or titanium, for example. In the following discussion and throughout this disclosure, the terms molecular sieve and zeolite will be used more or less interchangeably. One skilled in the art will recognize that the teachings relating to zeolites are also applicable to the more general class of materials called molecular sieves.

Depending on the context, all references herein to the "invention" may in some cases refer to certain specific embodiments only. In other cases it may refer to subject matter recited in one or more, but not necessarily all, of the claims. While the foregoing is directed to embodiments, versions and examples of the present invention, which are included to enable a person of ordinary skill in the art to make and use the inventions when the information in this patent is combined with available information and technology, the inventions are not limited to only these particular embodiments, versions and examples. Other and further embodiments, versions and examples of the invention may be devised without departing from the basic scope thereof and the scope thereof is determined by the claims that follow.

What is claimed is:

1. A molecular sieve catalyst comprising:
   a catalyst component; and
   a binder component providing mechanical support for the catalyst component:
   wherein said binder component is an ion-modified binder having at least one active metal species;
   wherein the ion-modified binder is capable of attachment to polar contaminants and thereby inhibit the contact of polar contaminants with the catalyst component;
   wherein metal ions make up 0.1% to 50% by weight of the ion-modified binder; and
   wherein the metal ions are chosen from the group consisting of Cu, Zn, Sn, Pb, Bi, Ba, Mn, and combinations thereof.

2. The catalyst according to claim 1, wherein the binder is composed primarily of amorphous silica or alumina.

3. The catalyst according to claim 1, wherein the metal ions make up 0.1% to 20% by weight of the ion-modified binder.

4. The catalyst according to claim 1, wherein the ion-modified binder makes up from 1% to 80% by weight of the catalyst.

5. The catalyst according to claim 1, wherein the ion-modified binder makes up from 5% to 60% by weight of the catalyst.

6. A zeolite catalyst comprising:
   a catalyst component; and
   a binder component providing mechanical support for the catalyst component:
   wherein said binder component is an ion-modified binder having at least one active metal species;
   wherein the ion-modified binder is capable of attachment to polar contaminants and thereby inhibit the contact of polar contaminants with the catalyst component;
   wherein metal ions make up 0.1% to 50% by weight of the ion-modified binder; and
   wherein the metal ions are chosen from the group consisting of Cu, Zn, Sn, Pb, Bi, Ba, Mn, and combinations thereof.

7. The catalyst according to claim 6, wherein the binder is composed primarily of amorphous silica or alumina.

8. The catalyst according to claim 6, wherein the metal ions make up 0.1% to 20% by weight of the ion-modified binder.

9. The catalyst according to claim 6, wherein the ion-modified binder makes up from 1% to 80% by weight of the catalyst.

10. The catalyst according to claim 6, wherein the ion-modified binder makes up from 5% to 60% by weight of the catalyst.

* * * * *